United States Patent
Littrup et al.

(10) Patent No.: US 7,128,738 B2
(45) Date of Patent: *Oct. 31, 2006

(54) METHOD AND SYSTEM FOR CRYOABLATING FIBROADENOMAS

(75) Inventors: Peter J. Littrup, Detroit, MI (US); Seth A. Stabinsky, Pleasanton, CA (US); Kevin Van Bladel, Livermore, CA (US); Lisa Zindel, Pleasanton, CA (US); Glenn Foy, Pleasanton, CA (US)

(73) Assignee: Sanarus Medical, Inc., Pleasanton, CA (US)

(*) Notice: Subject to any disclaimer, the term of this patent is extended or adjusted under 35 U.S.C. 154(b) by 127 days.

This patent is subject to a terminal disclaimer.

(21) Appl. No.: 10/941,511

(22) Filed: Sep. 14, 2004

(65) Prior Publication Data

US 2005/0033273 A1 Feb. 10, 2005

Related U.S. Application Data

(63) Continuation of application No. 10/264,930, filed on Oct. 4, 2002, now Pat. No. 6,789,545.

(51) Int. Cl.
*A61B 18/18* (2006.01)
(52) U.S. Cl. ...................................... 606/20
(58) Field of Classification Search ............ 606/20–26
See application file for complete search history.

(56) References Cited

U.S. PATENT DOCUMENTS

| 5,207,674 | A | | 5/1993 | Hamilton .................... 606/20 |
| 5,334,181 | A | * | 8/1994 | Rubinsky et al. ............. 606/22 |
| 6,015,390 | A | * | 1/2000 | Krag ........................ 600/549 |
| 6,032,675 | A | | 3/2000 | Rubinsky .................... 128/898 |
| 6,039,730 | A | * | 3/2000 | Rabin et al. ................. 606/23 |
| 6,074,412 | A | | 6/2000 | Mikus et al. ............... 607/105 |
| 6,123,702 | A | | 9/2000 | Swanson et al. .............. 606/34 |
| 6,235,018 | B1 | | 5/2001 | LePivert ..................... 606/20 |
| 6,251,105 | B1 | | 6/2001 | Mikus et al. ................. 606/22 |
| 6,494,844 | B1 | | 12/2002 | Van Bladel et al. ........ 600/567 |
| 6,527,765 | B1 | | 3/2003 | Kelman et al. ............... 606/22 |

FOREIGN PATENT DOCUMENTS

WO WO 01/97702 12/2001

* cited by examiner

*Primary Examiner*—Linda C. M. Dvorak
*Assistant Examiner*—Pete Vrettakos
(74) *Attorney, Agent, or Firm*—K. David Crockett, Esq.; Marc J. Frechett, Esq.; Crockett & Crockett

(57) ABSTRACT

A cryosurgical system adapted for treatment of fibroadenomas within the breast of a patient. The system includes cryoprobes and a control system which operates the cryoprobes to accomplish freezing in two stages, including a high power freeze and a low power freeze.

8 Claims, 2 Drawing Sheets

METHOD AND SYSTEM FOR CRYOABLATING FIBROADENOMAS

This application is a continuation of U.S. application Ser. No. 10/264,930 filed Oct. 4, 2002, now U.S. Pat. No. 6,789,545.

FIELD OF THE INVENTIONS

The inventions described below relate the field of cryosurgery and the treatment of breast disease.

BACKGROUND OF THE INVENTIONS

The methods and systems described below provide for optimal treatment of fibroadenomas. A fibroadenoma is a benign tumor found in women's breasts. They are small, solid, round, rubbery masses that are typically found in breast self-exams or mammography. Fibroadenomas are harmless, but may be painful, palpable and emotionally bothersome, and the may mask other lesions that would otherwise be visible to mammography. Fibroadenomas are removed to alleviate pain and to alleviate the emotional burden of living with a breast lump. Even when the breast lump is confirmed to be a benign fibroadenoma, many women elect removal for these reasons. Typically, fibroadenomas are removed by lumpectomy, which is an open surgical procedure. Open surgical recision requires a fairly large incision, creates an unsightly scar on the breast and a scar inside the breast that interferes with mammography, and it requires general anesthesia.

Sanarus, Inc. has proposed cryoablation of fibro-adenomas in its PCT publication WO0197702. As proposed in that publication, cryoablation entailed the commonly preferred double freeze-thaw cycle consisting of a 6 to 15 minute freezes followed by thawing until the internal cryoprobe temperature reaches 0° C. While that procedure is useful, the procedure described below provides suitable treatment with the advantages that a smaller iceball is created, it avoids ablating tissue surrounding the fibroadenoma that need not be ablated given the benign nature of the fibroadenoma, it limits the potential for damage to the skin overlying the fibroadenoma, and the resorption time for the ablated mass is greatly reduced.

SUMMARY

The methods and systems described below permit treatment of fibroadenomas with a minimally invasive cryosurgical procedure. The procedure entails use of a cryoprobe to cryoablate a fibroadenoma. Cryoablation is performed with a period of high power freezing, followed by a period of low power freezing, followed by a period of thawing, and a repetition of high power freezing and low power freezing, followed by thawing and/or warming of the cryoprobe. When accomplished with commercially available cryoprobes such our new Visica™ cryoprobes, which are adapted for partial duty cycle operation, the method entails a period of full power freezing, followed by a period of low duty cycle freezing, followed by a period of thawing, followed by a repetition of these steps.

Performance of the method is facilitated by a control system that allows a surgeon or technician to enter desired periods of full power freezing and reduced power freezing. The desired time for full power and reduced power freezing is selected based on the size of the fibroadenoma and empirical experience, and may be preprogrammed into the system control box. After entry of these parameters, the system operates automatically to apply cooling to the fibroadenoma as desired by the surgeon. The progress of the cryosurgery may be monitored with ultrasound and thermocouples.

DETAILED DESCRIPTION OF THE INVENTIONS

Figure 1:
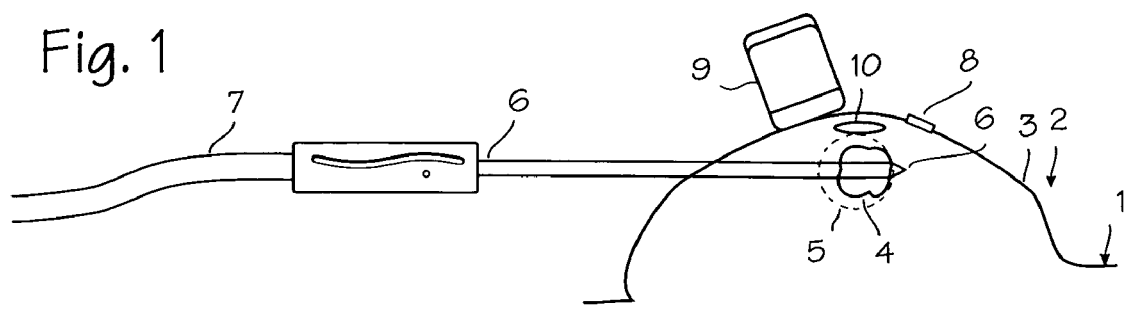
FIG. 1 illustrates the cryosurgical procedure for treating benign tumors in the breast.

FIG. 1 illustrates the cryosurgical procedure for treating benign tumors in the breast. The patient 1 and the patient's breast 2 and skin 3 of the breast are shown schematically. The fibroadenoma 4 is located within the breast, surrounded by soft tissue and fatty tissue. The fibroadenoma is a well-defined, hard mass ranging in size from 3 to 40 mm in diameter. The purpose of the procedure is to form an iceball 5 (the frozen mass of breast tissue) around the fibroadenoma, after which the natural healing processes of the body will result in resorption of the fibroadenoma by the patient's body. The iceball is formed with a cryoprobe 6, which, as illustrated, is inserted through the skin and intervening breast tissue into the fibroadenoma, so that the distal tip extends through the fibroadenoma. A gas supply hose 7 is attached to the cryoprobe and serves to supply high-pressure gas to the cryoprobe. The cryoprobe may include a temperature sensor, which directly or indirectly measures the temperature of the cryoprobe. A temperature sensor 8 may be used during the surgery to monitor skin temperature, so that surgeons can avoid causing frost-bite on the patient's skin. An ultrasound probe 9 is used during the procedure to visualize the formation, growth, and melting of the iceball that is formed within the breast when the cryoprobe is energized. The iceball is highly echogenic, so that its formation is very clearly visualized. The image of the iceball is displayed on a display screen provided with the ultrasound probe. An insulating mass 10 of saline or other inert substance may be injected into the breast, between the fibroadenoma and the skin to protect the skin from freezing when the fibroadenoma is frozen.

The cryoprobe may be our Visica™ cryoprobe, a Cryocare® cryoprobe, a Seednet™ or Cryohit™ cryoprobe, or any other cryoprobe. These cryoprobes are Joule-Thomson cryoprobes which provide cooling from the expansion of argon gas in the tip of the cryoprobe. Gas supply is typically provided at about 3000 psi, and is controlled with solenoid valves that can be cycled to control the "duty cycle" of the system. Duty cycle refers to the percentage of time that gas is supplied to the tip of the cryoprobe, expressed as a percentage, and controlled typically in ten second time frames (so that a 50% duty cycle indicates that gas is supplied for 5 seconds out of every ten second period of operation, and a 10% duty cycle indicates that gas is supplied for 1 second out of every ten second period of operation). These cryoprobes will also effect warming of tissue if supplied with a warming gas (helium) which warms upon expansion in the tip of the cryoprobe. Other cryoprobes which use liquid nitrogen flowing through the probe may also be used with the procedure. The temperature probe and ultrasound probe may be of any make.

To accomplish the procedure, the cryoprobe is operated for two cycles of high power freezing, low power freezing, with a thawing period interposed between the cycles and a warming period provided after the second freezing cycle. The periods of high power freezing, low power freezing, and thawing are selected depending on the size of the fibroadenoma. With experimentation, we have empirically determined the following freeze periods for fibroadenomas of various sizes:

| Fibroadenoma Longest Diameter | Freeze Cycle 1 | Passive Thaw | Freeze Cycle 2 | Warm Cycle |
|---|---|---|---|---|
| <1 cm | 2 min HI Freeze, 0 min LO Freeze | 2 min. | 2 min HI Freeze, 0 min LO Freeze | 1 min. |
| 1.0–1.5 cm | 2 min HI Freeze, 4 min LO Freeze | 6 min. | 2 min HI Freeze, 4 min LO Freeze | 1 min. |
| 1.6–2.0 cm | 3 min HI Freeze, 5 min LO Freeze | 8 min. | 3 min HI Freeze, 5 min LO Freeze | 1 min. |
| 2.1–2.5 cm | 5 min HI Freeze, 5 min LO Freeze | 10 min. | 5 min HI Freeze, 5 min LO Freeze | 1 min. |
| 2.6–3.0 cm | 6 min HI Freeze, 4 min LO Freeze | 10 min. | 6 min HI Freeze, 4 min LO Freeze | 1 min. |
| 3.1–3.5 cm | 8 min HI Freeze, 2 min LO Freeze | 10 min. | 8 min HI Freeze, 2 min LO Freeze | 1 min. |
| 3.6–4.0 cm | 10 min HI Freeze, 0 min LO Freeze | 10 min. | 10 min HI Freeze, 0 min LO Freeze | 1 min. |

As indicated in the table, a fibroadenoma smaller than 1 cm in diameter is treated with two freezing cycles consisting of 2 minutes of high power freezing and without a period of low power freezing, and 2 minutes of passive thawing between the freezing cycles. A fibroadenoma of 1–1.5 cm diameter is treated by two cycles consisting of 2 minutes of high power freezing, 4 minutes of low power freezing, with 6 minutes of passive thawing between the cycles and a 1 minute warming period following the second freeze cycle. A fibroadenoma of 1.6 to 2.0 cm diameter is treated by two cycles consisting of 3 minutes of high power freezing, 5 minutes of low power freezing, with 10 minutes of passive thawing between the freezing cycles and followed by 1 minute of warming operation after the two freezing cycles. A fibroadenoma of 2.1 to 2.5 cm diameter is treated by two cycles consisting of 5 minutes of high power freezing, 5 minutes of low power freezing, with 10 minutes of passive thawing between the freezing cycles and followed by 1 minute of warming operation after the two freezing cycles. A fibroadenoma of 2.6 to 3.0 cm diameter is treated by two cycles consisting of 6 minutes of high power freezing, 4 minutes of low power freezing, with 10 minutes of passive thawing between the freezing cycles and followed by 1 minute of warming operation after the two freezing cycles. A fibroadenoma of 3.1 to 3.5 cm diameter is treated by two cycles consisting of 8 minutes of high power freezing, 2 minutes of low power freezing, with 10 minutes of passive thawing between the freezing cycles and followed by 1 minute of warming operation after the two freezing cycles. A fibroadenoma of 3.6 to 4.0 cm diameter is treated by two cycles consisting of 10 minutes of high power freezing without a period of low power freezing, with 10 minutes of passive thawing between the freezing cycles and followed by 1 minute of warming operation after the two freezing cycles. This algorithm for treatment is sufficient for treating fibroadenomas up to 4 cm. Larger fibroadenomas may require additional procedures.

These time periods may be varied to accomplish other regimens falling under the general description of two freezing cycles comprising a high power freeze and a low power freeze with a thawing period between the freezing cycles. It is specifically contemplated that they be adjusted to account for cryoprobes of differing cooling power or cryoprobes from different manufacturers, and that the fibroadenoma size ranges be condensed or expanded as clinical experience dictates. Also, the thawing period may be augmented by application of warming gas to promote thawing. Particularly, low duty cycle application of thawing gas during the THAW period may be employed.

Figure 2:
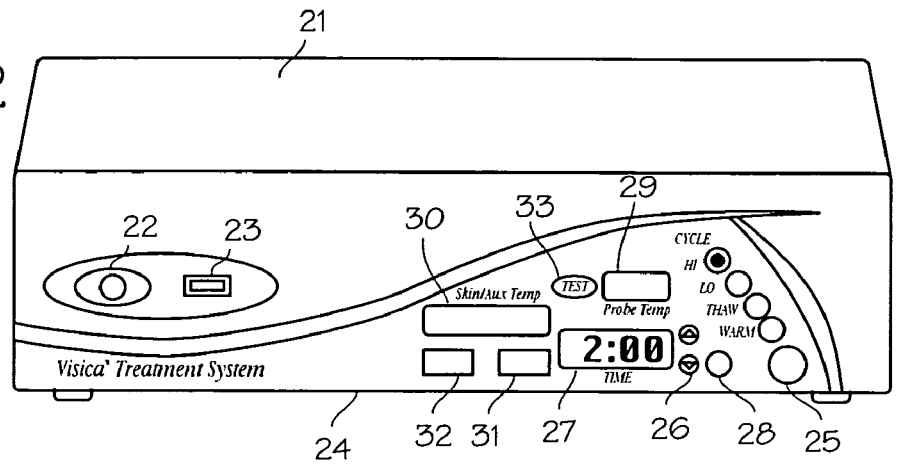
FIG. 2 illustrates the control box and user interface for controlling a cryoprobe to accomplish the cryoablation of a fibroadenoma.

FIG. 2 illustrates the control box which is used to control the cryoprobes to accomplish the procedure described above. The control box 21 houses the required computer, microprocessor, or other control circuit, the displays and operator input devices necessary to accept operator input and the computer controlled valves, system input devices, to control the cryoprobe according to the operator's input. The control box includes a gas connection 22 for connecting the gas supply hose to a valve inside the box which controls cooling gas supply to the cryoprobe. Various valves and electromechanical controls within the control box comprise a fluid supply assembly which serves to operably connect the cryoprobe to a cooling fluid source and to a warming fluid source. The cooling fluid is preferably high-pressure argon gas, and the warming fluid is preferably high-pressure helium gas. A cryoprobe thermocouple connector 23 is provided for connecting the thermocouple typically installed in the cryoprobe to the control box.

The display and input panel 24 includes the various input buttons and displays used by the operator. These include cryoprobe mode selection buttons for selecting HI and LO, THAW, or WARM operation and buttons for input of time parameters by the operator. The buttons or associated LEDs illuminate or otherwise alter their appearance to indicate that the operator has selected that mode for time input (in the input mode of the system) or to indicate the operating mode of the cryoprobe (in the operating mode of the system). A start/stop button 25 provides a means for the operator to initiate the programmed sequence of cooling and thawing after inputting desired parameters. Freezing time input buttons 26 provide a means for the operator to enter procedure times for the selected cryoprobe mode selection, and the operator-entered procedure time is displayed in the procedure time display window 27 (a reset button 28 can be used to reset the entered procedure time, to exit the programming mode, or restart the computer system which controls the interface). Temperature indication windows 29 and 30 display the cryoprobe temperature (as measured by the thermocouple in the cryoprobe) and skin temperature (as measured by the skin mounted temperature sensor 8, or perhaps a thermocouple inserted under the skin). The skin temperature sensor and separate thermocouple are connected to the control box through connectors 31 and 32. The connectors may be connected to thermocouples as desired by the operator.

The test/flush button 33 controls a test function which the control system is programmed to perform prior to freezing operation. Depending the operating mode of the system, the test/flush button, when activated by the operator, will initiate a short period of warming gas flow sufficient to flush the probe of any moisture (10 to 20 seconds) followed by a short period of cooling gas flow (20–60 seconds) sufficient to form an iceball in water. In conjunction with this operation, the operator can submerge the cryoprobe tip in water and ensure that the probe tip does not leak during flushing and that an iceball forms during cooling gas flow. The test iceball is then melted so that the cryoprobe is ready for use. When the system enters the freeze operation mode, the operator's use of the test/flush button will initiate warming gas flow when activated by the operator. This provides the operator with a means for interrupting cooling operation should it be necessary to protect skin from freezing or remove the cryoprobe immediately for any reason.

Figure 3:
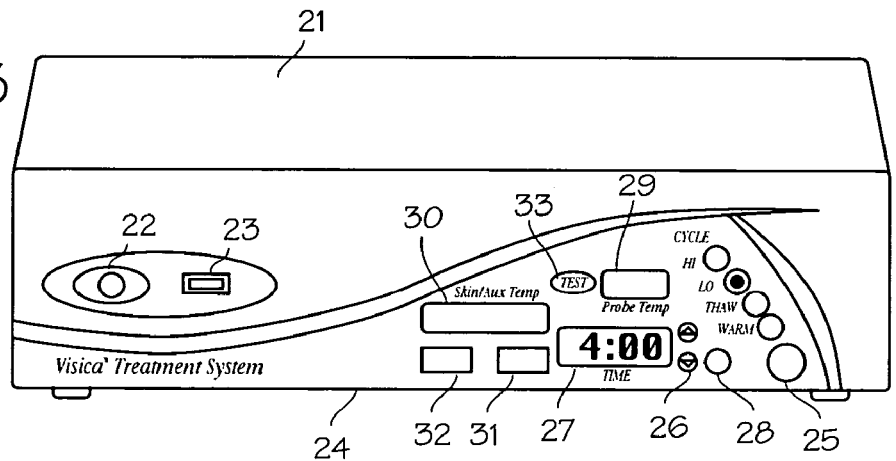
FIGS. 3, 4, 5, 6 and 7 illustrate various operations of the fibroadenoma cryoablation system.

The sequence of operation of the system is illustrated in FIG. 2 and FIGS. 3 through 7. Prior to operation of the system, the operator must determine the size of the fibroadenoma to be treated. These illustrations assume that the operator has determined that the fibroadenoma is between 1 and 1.5 cm in diameter. In FIG. 2, the operator has started the system, and the system has entered its program mode. The operator has pushed the HI mode selection button, and the control system has illuminated the HI mode selection button and will now interpret time entered into the procedure time as the desired time for HI mode operation. The operator then enters the desired time for HI mode operation, and the system stores this value as the desired duration of HI mode operation. In this case, the operator has entered 2 minutes for HI power freezing, which is the empirically pre-determined optimal HI power freezing time for treat the 1–1.5 cm fibroadenoma. In FIG. 3, the operator has selected the LO mode selection button and the control system has illuminated the LO mode selection button and will now interpret time entered into the procedure time as the desired time for LO mode operation. The operator then enters the desired time for LO mode operation, and the system stores this value as the desired duration of LO mode operation. In this case, the operator has entered 4 minutes for LO power freezing, which is the empirically pre-determined optimal LO power freezing time for treat the 1–1.5 cm fibroadenoma.

Figure 4:
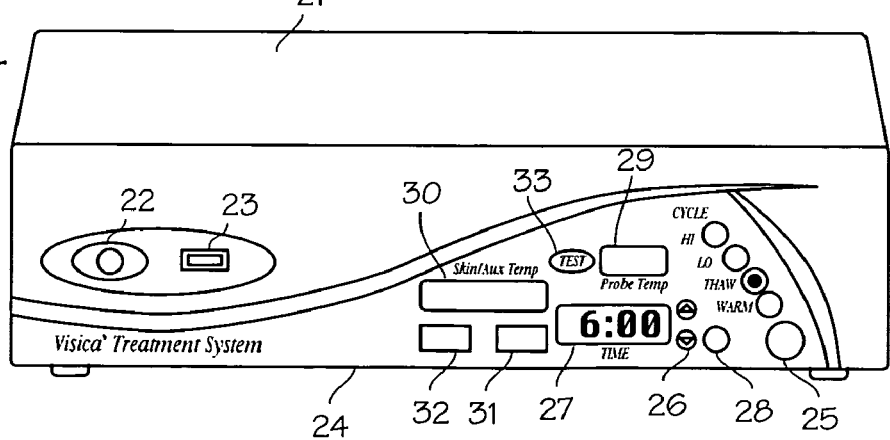

The next illustrated step may be accomplished by the operator, or may be accomplished automatically by the control system. If accomplished by the operator, then, as shown in FIG. 4, the operator selects the THAW mode selection button and the control system illuminates the THAW mode selection button and interprets the time entered by the operator into the procedure time as the desired time for THAW mode operation. The operator enters the desired time for THAW mode operation, and the system stores this value as the desired duration of THAW mode operation. In this case, the operator has entered 6 minutes for THAW operation, in which the system does not supply gas to the cryoprobe and the iceball is permitted to thaw (which happens fairly quickly, given that the iceball is subject to body temperature and blood flow in the surrounding tissue), which is the empirically pre-determined optimal THAW time for treat the 1–1.5 cm fibroadenoma. We currently prefer to have the system automatically set the THAW time, and have empirically determined that a THAW time equal to the combined HI and LO freeze times, which in this case is 6 minutes, ensures complete thawing without entailing undue delay in proceeding to the second freeze cycle. Accordingly, the control system is programmed to calculate and set the THAW time based on the entered freeze times.

After the operator has entered the HI and LO freeze times (and, optionally, the THAW time), and the cryoprobe and cryoprobe thermocouple have been connected to the control box, and the cryoprobe has been flushed and tested, the system will accept input from the start/stop button 25 as the operator's input, and start freezing operations in accordance with the operator entered parameters. If the cryoprobe is disconnected after testing, the system will reset itself and require reentry of freeze time parameters. This feature may incorporate a short delay of about 5 seconds, such that disconnection in excess of 5 seconds will result in a reset, while disconnects of less than five seconds will be tolerated and the system will permit the operator to initiate the freezing operation after such a short disconnection.

Figure 5:
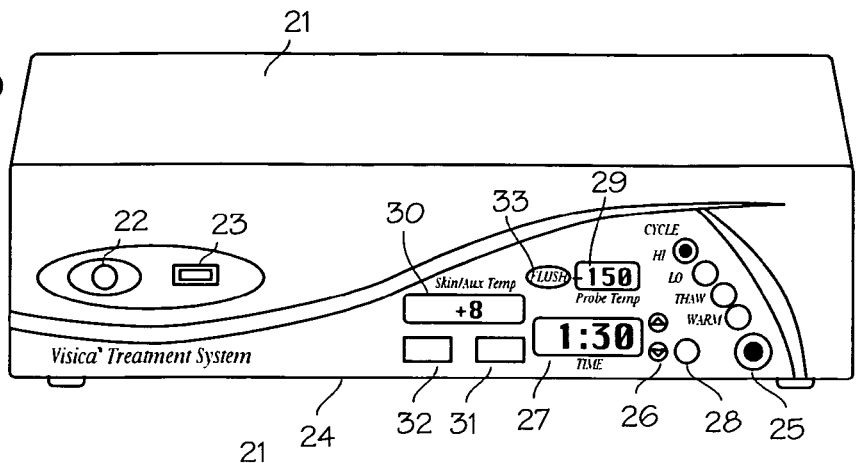
Figure 6:
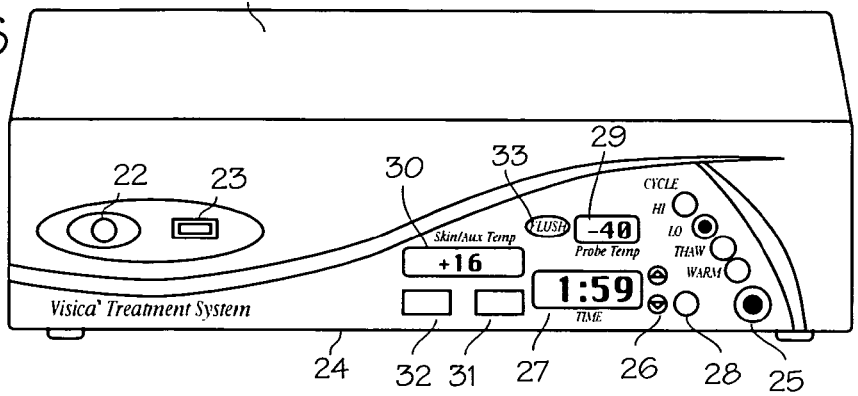
Figure 7:
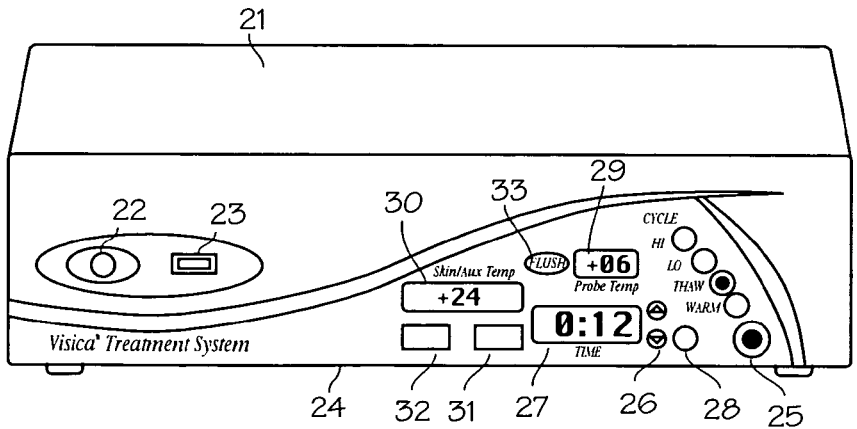

As shown in FIG. 5, the system indicates that it is operating in the HI freeze mode by illuminating the HI mode selector button (or an associated indicator). The control system provides output to the procedure time window to show either the elapsed or remaining HI mode operation time. The test/flush button has entered the flush mode. The temperature as measured at the cryoprobe thermocouple is displayed in the cryoprobe temperature window 29 and the skin temperature (or temperature measured by separate probe) is displayed in the skin/aux temperature display window 8. In this illustration, a few seconds of cooling have elapsed and the system indicates that 1 minute and 30 seconds of HI mode operation remain, the cryoprobe temperature has reached −150° C., and the skin temperature has reached +16° C. When HI mode operation is complete, the system immediately enters the LO mode operation, and the display associated with LO mode operation is illustrated in FIG. 6. In FIG. 6, the display indicates that the control system has entered into the LO mode operation, and the procedure time window indicates that 1 minute, 59 seconds of LO mode operation is remaining. The probe temperature display will show that the probe is warming, but the low duty cycle operation of the cryoprobe is sufficient to maintain the iceball at substantially the same size obtained in the HI mode of freezing. Cryoprobe temperature rises, as indicated, but does not rise above about −45° C. (in the specific system described herein) to keep the iceball cold without permitting substantial growth of the iceball (cryoprobe temperature should cycle between about −100° C. and −45° C.). In FIG. 7, the display indicates that the control system has entered into the THAW mode of operation. The THAW mode of 6 minutes is almost complete, and the cryoprobe temperature has risen substantially, and the skin temperature has risen to near normal (if it has cooled at all during the freezing process).

After this THAW period, the control system will repeat the HI freeze and LO freeze operations, followed by a warming operation which is automatically set at a preselected period of 30 to 60 seconds. Operation in the WARM mode permits quick removal of the cryoprobe from the breast after the full procedure has been accomplished. The control system can also be programmed to provide an alarm or visual indication when the cryoprobe reaches a predetermined temperature of about +10° C., and to shut off warming gas flow should the cryoprobe temperature approach the temperature which would cause additional injury to the breast (shut off at about +30° C. will ensure that the cryoprobe temperature does not reach thermally damaging temperature of +45° C.). Operation in the WARM mode is indicated on the display panel by the WARM mode indicator. An additional feature that is programmed into the control box controls the warming mode to automatically clear the cryoprobe in the case of clogging or reduced cooling gas flow. During cooling operations, should cooling gas flow be reduced unexpectedly (as from a blockage causes by freezing inside the probe), the system can identify the blockage and clear it automatically. To do this, the control system tracks the mode of operation and the expected temperature of the cryoprobe. If the temperature should rise (or fail to drop) when cooling gas it flowing, the control system automatically stops cooling gas flow, initiates warming gas flow for a brief period, and then re-initiates cooling gas flow (the time for cooling may be amended by the control system to recover the time lost to clearing the blockage). The brief period of warming gas flow (15 to 90 seconds) is sufficient to melt most ice blockages formed within the probe. Flow rate can be monitored indirectly by sensing the temperature of the cryoprobe, or by sensing the exhaust pressure of the cryoprobe, or it may be monitored directly with flow meters anywhere in the gas flow path.

Figure 8:
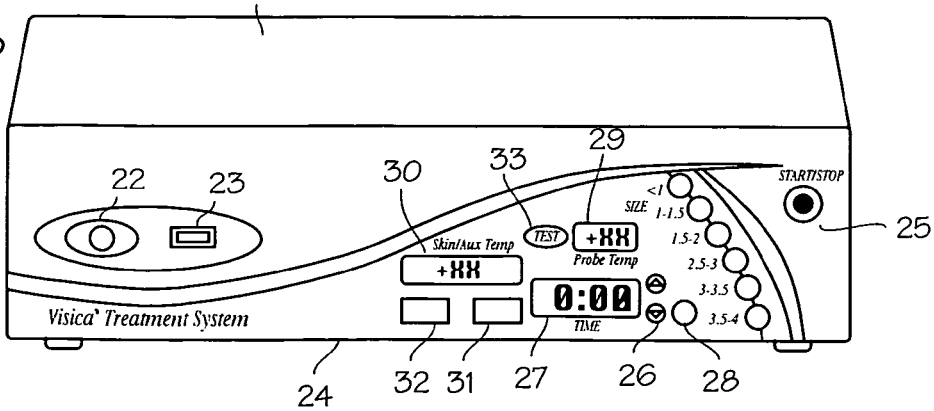
FIG. 8 illustrates a fibroadenoma cryoablation system designed to operate with predetermined cycle times.

FIG. 8 illustrates a system designed to operate with pre-set freeze cycles. In this system, the empirically determined optimal HI freeze, LO freeze, and THAW and WARM times associated with fibroadenomas falling within selected size ranges are programmed into the control system. Input of the predetermined HI freeze and LO freeze time period will be accomplished by means of programming the computer, microprocessor or control circuit. The interface comprises mode selection buttons which correspond to the selected fibroadenoma sizes, rather than freezing modes. After measuring the fibroadenoma, the operator selects the matching button, presses the start/stop button, and the system automatically selects the predetermined time periods for HI, LO and THAW operations, and operates the cryoprobe accordingly. The test/flush operations and the WARM mode are also available in this embodiment.

The method of treatment can be implemented on cryosurgical systems of varying design, modified as necessary to achieve the objectives of the method. For example, though the LO mode of operation requires a 10% duty cycle (1 second of gas flow every ten seconds) in a Cryocare® system using a Cryocare® probe, other systems may be limited to duty cycles necessary to maintain sensed iceball temperature at or below –10° C. If implemented with a nitrogen powered cryoprobe, this limitation can be met by pulsing the flow of nitrogen, or by throttling the flow of nitrogen, to allow the iceball to warm without permitting the iceball to recede. In a Joule-Thomson system, the reduction in freezing power can be accomplished by reducing the pressure of cooling gas supplied to the probes, rather than providing intermittent flow of gas supplied at a constant high pressure. The display and input panel may be implemented as shown, with digital counters and pushbutton inputs, or through a touch-screen, or through a desktop computer and computer monitor. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A system for cryoablating a fibroadenoma within the breast of a patient comprising:
   a cryoprobe adapted for percutaneous insertion through the skin of the breast and into the fibroadenoma, said cryoprobe adapted to provide cooling at a first power level and a second power level, where the first power level provides cooling to a first cryogenic temperature and the second power level provides cooling to a second cryogenic temperature which is higher than the first cryogenic temperature;
   a fluid supply assembly operably connected to the cryoprobe and adapted to provide cooling fluid to the cryoprobe;
   a control system for controlling operation of the cryoprobe and fluid supply assembly in response to operator input;
   input means for entry of a first time desired for operation of the cryoprobe at the first power level and for entry of a second time desired for operation of the cryoprobe at the second power level;
   wherein the control system controls the cryoprobe to freeze the fibroadenoma, and is programmed to operate the cryoprobe at the first power level for a period equal to the first time, and thereafter operate the cryoprobe at the second power level for a period equal to the second time, and thereafter to shut off the cryoprobe to provide a predetermined thawing period that equals the sum of the first time and second time, and thereafter operate the cryoprobe at the first power level for a period equal to the first time, and thereafter operate the cryoprobe at the second power level for a period equal to the second time.

2. The system of claim 1 wherein:
   the input means comprises a display and input panel comprising time input means and a display for indicating time entered by an operator, and mode selection means for selecting a mode of cryoprobe operation for which time input pertains; and
   the control system accepts input from the time input means regarding the entered first time and the entered second time, and determines the thawing period based on the entered first time and second time.

3. The system of claim 1 wherein:
   the fluid supply assembly is further adapted to provide a warming fluid to the cryoprobe; and
   the control system is programmed to provide warming flow to the cryoprobe for a predetermined period after operating the cryoprobe to freeze the fibroadenoma.

4. The system of claim 1 wherein:
   the control system and fluid supply assembly are adapted to supply the cryoprobe with cooling fluid at varying duty cycles, and the control system is programmed to operate the cryoprobe at a first duty cycle to provide cooling at the first power level and to operate the cryoprobe at a second duty cycle to provide cooling at the second power level.

5. The system of claim 1 wherein:
   the control system and fluid supply assembly are adapted to supply the cryoprobe with cooling fluid at varying duty cycles, and the control system is programmed to operate the cryoprobe at a 100% duty cycle to provide cooling at the first power level and to operate the cryoprobe at a 10% duty cycle to provide cooling at the second power level.

6. The system of claim 1 wherein:
   the control system and fluid supply assembly are adapted to supply the cryoprobe with cooling fluid at varying flow rates, and the control system is programmed to operate the cryoprobe at a first flow rate to provide cooling at the first power level and to operate the cryoprobe at a second flow rate to provide cooling at the second power level.

7. The system of claim 1 wherein:
   the first power level provides high power freezing and the second power level provides low power freezing, and the freezing and thawing periods are selected based on the size of the fibroadenoma.

8. The system of claim 1 wherein:
the control system is adapted to operate with preset freeze cycles by empirically determining the optimal high power and low power freezing periods for any given cryoprobe, and selecting the high power period and low power period to correspond to the empirically determined optimal high power and low power freezing points.

* * * * *